United States Patent
Manigel et al.

(10) Patent No.: US 10,682,485 B2
(45) Date of Patent: Jun. 16, 2020

(54) ANESTHETIC DISPENSING DEVICE (71) Applicant: Drägerwerk AG & Co. KGaA, Lübeck (DE)

(72) Inventors: Jürgen Manigel, Hamburg (DE); Uwe Bartels, Lübeck (DE); Klaus Radomski, Lübeck (DE)

(73) Assignee: DRÄGER WERK AG & CO. KGAA, Lübeck (DE)

( * ) Notice: Subject to any disclaimer, the term of this patent is extended or adjusted under 35 U.S.C. 154(b) by 973 days.

(21) Appl. No.: 14/982,500

(22) Filed: Dec. 29, 2015

(65) Prior Publication Data
US 2016/0193441 A1 Jul. 7, 2016

(30) Foreign Application Priority Data
Jan. 2, 2015 (DE) .................. 10 2015 000 175

(51) Int. Cl.
*A61M 16/10* (2006.01)
*A61M 16/20* (2006.01)
(Continued)

(52) U.S. Cl.
CPC ...... *A61M 16/1075* (2013.01); *A61M 16/024* (2017.08); *A61M 16/18* (2013.01);
(Continued)

(58) Field of Classification Search
CPC ............ A61M 16/1075; A61M 16/024; A61M 16/18; A61M 16/204; A61M 16/01;
(Continued)

(56) References Cited

U.S. PATENT DOCUMENTS 3,671,024 A * 6/1972 Breiling ............... A61M 16/18
128/203.14
4,059,657 A * 11/1977 Hay ..................... A61M 16/18
128/203.25
(Continued)

FOREIGN PATENT DOCUMENTS

CN 102355921 A 2/2012
DE 689 18 941 T2 5/1995
(Continued)

*Primary Examiner* — Timothy A Stanis
*Assistant Examiner* — Margaret M Luarca
(74) *Attorney, Agent, or Firm* — McGlew and Tuttle, P.C.

(57) ABSTRACT

An anesthetic dispensing device (1), to which a carrier gas stream is fed for enriching with anesthetic, has the gas stream split into two partial gas streams, one of which flows through a bypass channel (7) unchanged and the other of which is fed to an evaporation chamber (9), where the partial gas stream is saturated with anesthetic. In a mixing point (6), both partial gas streams are mixed to form an anesthetic gas stream, which leaves the anesthetic dispensing device through the anesthetic gas outlet (4). A control unit (2) is provided that is configured to generate a control signal for an electric motor drive (14) for adjusting the valve opening of the valve element (15) on the basis of a concentration of the anesthetic in the anesthetic gas needed at the anesthetic gas outlet (4) and at least one temperature-specific correction factor.

17 Claims, 6 Drawing Sheets

(51) Int. Cl.
*A61M 16/18* (2006.01)
*A61M 16/00* (2006.01)

(52) U.S. Cl.
CPC ... *A61M 16/204* (2014.02); *A61M 2202/0241* (2013.01); *A61M 2205/3334* (2013.01); *A61M 2205/3365* (2013.01); *A61M 2205/3368* (2013.01); *A61M 2205/52* (2013.01)

(58) Field of Classification Search
CPC .. A61M 16/104; A61M 16/12; A61M 16/201; A61M 16/202
See application file for complete search history.

(56) References Cited

U.S. PATENT DOCUMENTS

| | | | | |
|---|---|---|---|---|
| 4,436,674 A * | 3/1984 | McMenamin | ........... | B01J 4/008 118/692 |
| 4,637,385 A * | 1/1987 | Rusz | ........... | A61M 16/024 128/204.21 |
| 4,657,710 A * | 4/1987 | Smith | ........... | A61M 16/18 261/46 |
| 4,770,168 A * | 9/1988 | Rusz | ........... | A61M 16/18 128/203.12 |
| 4,798,689 A * | 1/1989 | Heim | ........... | A61M 16/18 128/203.14 |
| 5,649,531 A * | 7/1997 | Heinonen | ........... | A61M 16/18 128/203.12 |
| 5,771,884 A * | 6/1998 | Yarnall | ........... | A61M 16/20 128/204.19 |
| 7,438,072 B2 * | 10/2008 | Izuchukwu | ........... | A61M 16/0051 128/203.12 |
| 9,199,056 B2 * | 12/2015 | Loncar | ........... | A61M 16/01 |
| 2010/0242962 A1 * | 9/2010 | Chen | ........... | A61M 16/18 128/203.26 |

FOREIGN PATENT DOCUMENTS

| | | |
|---|---|---|
| DE | 692 08 836 T2 | 10/1996 |
| DE | 10 2005 032 154 B3 | 2/2007 |
| EP | 0 545 567 A1 | 6/1993 |

* cited by examiner

ANESTHETIC DISPENSING DEVICE

CROSS REFERENCE TO RELATED APPLICATIONS

This application claims the benefit of priority under 35 U.S.C. § 119 of German Patent Application 10 2015 000175.2 filed Jan. 2, 2015, the entire contents of which are incorporated herein by reference.

FIELD OF THE INVENTION

The present invention pertains to an anesthetic dispensing device with a carrier gas inlet and with an anesthetic gas outlet, which are connected to one another via a bypass channel and via a dispensing channel arranged parallel hereto in terms of flow. An anesthetic-filled evaporation chamber, through which carrier gas flows, is connected to the dispensing channel, such that the carrier gas is enriched with anesthetic and subsequently flows through the dispensing channel to the anesthetic gas outlet. The variation of the carrier gas volume flow flowing through the evaporation chamber is carried out by means of a valve element, the valve opening of which can be changed as needed.

BACKGROUND OF THE INVENTION

Anesthetic dispensing devices with an evaporation chamber are frequently used in conjunction with anesthesia apparatuses in order to enrich a carrier gas with a volatile anesthetic. In the liquid state, the anesthetic is filled into the evaporation chamber, which is usually equipped with a wick device, which becomes saturated with the anesthetic and on its surface finally discharges the evaporating anesthetic liquid to the carrier gas flowing through the evaporation chamber. The concentration of the anesthetic in the anesthetic gas fed to the patient must be adapted as a function of the kind of anesthesia as well as the progress of the operation. A hand wheel, by means of which the dispensing unit can be adjusted in a specific manner in the anesthetic evaporator, is provided for this purpose in prior-art anesthetic evaporators.

An anesthetic dispensing device of this type with evaporation chamber, in which the portion of the gaseous anesthetic in the anesthetic gas can be adjusted in a specific manner, is known from DE 25 07 261 A1. The principal portion of the carrier gas stream at first flows in a bypass line past the evaporation chamber. By contrast, a small portion of the carrier gas is fed by a branching of the carrier gas stream into the evaporation chamber, in which it is enriched with the anesthetic until it is saturated and finally flows out of the evaporation chamber via an adjustable dispensing gap. The part of the carrier gas stream thus enriched with anesthetic is in turn added to the part of the carrier gas stream, which leaves the bypass channel unchanged, in order to thus generate the anesthetic gas stream needed for the anesthesia of the patient. The concentration of the anesthetic in the anesthetic gas stream can be adjusted in this connection by means of a variation of the dispensing gap in the dispensing unit, with the portion of the anesthetic in the anesthetic gas being changed by means of changing the dispensing gap width in a specific manner. Via the anesthetic gas outlet, this gas is first fed to an anesthesia apparatus and finally fed to the patient to be treated.

The dispensing gap described is designed as a ring gap which is formed by a flat surface of a hollow ring body and the flat surface of a hollow cylinder arranged in the hollow ring body. Temperature-related changes in the dispensing gap can be caused by temperature fluctuations in the surrounding area of the anesthetic dispensing device as well as because of the cooling off of the evaporation chamber, which brings about a lowering of the saturation concentration of the anesthetic vapor. To also compensate temperature-related changes in the dispensing gap, a temperature compensation is provided in the anesthetic dispensing device described in DE 25 07 261 A1. For this purpose, the hollow cylinder and the hollow ring body are made of different materials, with the hollow cylinder having a smaller coefficient of thermal expansion than the hollow ring body. In case of temperature changes in the evaporation chamber, the different coefficients of thermal expansion bring about a path of the flat surface, with which the height of the ring gap is changed. The height of the ring gap and thus the free cross section can be changed by providing suitable adjusting screws for adjusting via the ring body.

Furthermore, an anesthetic dispensing device, which has an especially low-friction adjustment of a dispensing cone with respect to a cone sleeve, is known from DE 10 2005 032 154 B3. In this case, the dispensing cone is fastened in a manner capable of performing strokes with respect to the cone sleeve by means of two membrane elements spaced apart in parallel. A movement of the dispensing piston is carried out mechanically either by means of a hand wheel or by means of an electric direct drive.

It is problematic in the solutions known from the state of the art that, on the one hand, that a temperature compensation is accomplished with comparatively complicated measures. In particular, the selection of suitable materials as well as the manufacture and the adjustment of correspondingly accurately adjustable dispensing elements require a considerable technical effort and are economically costly. In order to guarantee a corresponding temperature compensation, it is known to adjust an air stream that flows around the dispensing unit by means of mechanically acting mechanisms in a suitable manner.

SUMMARY OF THE INVENTION

Based on the technical solutions known from the state of the art as well as the problems described above, a basic object of the present invention is to provide a dispensing unit for the dispensing of an anesthetic in a gas stream, in which an accurate temperature compensation can be implemented with comparatively simple means. In particular, the temperature compensation shall be achieved in such a way that no further adjusting or calibrating measures are needed during the startup and the operation of a corresponding device. Furthermore, the adjustment of the desired anesthetic concentration shall be possible with simple means for the user and shall nevertheless ensure a highly accurate dispensing of anesthetic.

An anesthetic dispensing device, with which the object described above is provided according to the invention. The present invention pertains to an anesthetic dispensing device with a carrier gas inlet and with an anesthetic gas outlet, which are connected via a bypass channel and a dispensing channel arranged parallel hereto in terms of flow. Furthermore, an anesthetic-filled evaporation chamber is provided, which enriches gas flowing in with anesthetic, such that carrier gas enriched with anesthetic flows from the evaporation chamber to the anesthetic gas outlet. Furthermore, the anesthetic dispensing device has a valve element, the valve opening of which can be changed for variation of a volume flow of the carrier gas to be enriched with anesthetic, flowing through the evaporation chamber. An anesthetic dispensing device designed according to the present invention is characterized in that a control unit is provided, by means of which a control signal can be generated for an electric motor drive for adjusting the valve opening of the valve element on the basis of a concentration of the anesthetic in the anesthetic gas needed at the anesthetic gas outlet and at least one temperature-specific correction factor. The anesthetic concentration needed thus represents a desired value, which shall be reached by means of suitable adjustment.

The electric motor drive provided according to the present invention is thus actuated in such a way that the anesthetic concentration needed is adjusted by taking into account a temperature in the area surrounding the anesthesia apparatus and/or a temperature prevailing in the evaporation chamber. In this case, the valve element is adjusted by the electric motor drive in such a way that the valve opening has the dispensing gap necessary for the flowthrough of the volume flow needed. Because of providing at least one temperature-specific correction factor, it is advantageously possible to take into account especially temperature changes, which are adjusted in the evaporation chamber because of the evaporation of the anesthetic taking place there during the adjustment of the valve opening. The use of an electric motor drive, which is actuated in a suitable manner, thus makes possible an accurate dispensing with temperature compensation that is comparatively simple to achieve at the same time. According to a special variant, the electric motor drive is designed as a stepping motor or as a brushed or brushless direct-current motor, and a gear, e.g., in the form of a one-stage or two-stage planet gear, may be provided for reinforcing the torque between the valve element and the electric motor.

In a preferred embodiment of the present invention, provisions are made for the control unit to be connected to a memory unit, in which at least one characteristic is stored for the determination of the temperature-specific correction factor. Preferably, the temperature-specific correction factor in this case has been formed by taking into account an absolute temperature and/or a temperature change in the surrounding area of the dispensing device and/or in the evaporation chamber. It is especially advantageous in this connection when, in connection with the manufacture of an anesthetic dispensing device designed according to the present invention, corresponding apparatus-specific characteristics are recorded and are stored in the memory unit, to which the control unit can have access during the operation of the anesthetic dispensing device. Corresponding characteristics thus only have to be recorded and stored once and can thus always be used during the ongoing operation, without additional calibration steps being necessary for ensuring a temperature compensation.

The temperature sensor at least one of detecting a value of an absolute temperature, detecting a value of a change in temperature in the evaporation chamber and detecting a value of a surrounding area temperature of the evaporation chamber. The temperature sensor transmits the detected value at least indirectly to the control unit. The temperature sensor being arranged at least in some areas in or at the evaporation chamber, whereby the temperature-specific correction factor is generated taking the detected value into account.

The valve element designed according to the present invention preferably has a dispensing cone arranged in a movable manner, which is mounted in a movable manner with respect to a cone sleeve. A ring-shaped dispensing gap, which can be changed as needed and which guarantees an accurate dispensing of anesthetic into the carrier gas stream, is provided by means of such a dispensing cone. To implement the necessary adjustment of the dispensing means concentration by means of such a dispensing cone, the angular position of the motor shaft in active connection with the dispensing cone is especially monitored. Such a motor shaft can selectively be used directly or via the intermediary of a gear with a valve element, especially with a preferably used dispensing cone. According to an advantageous variant of the present invention, it is therefore conceivable that a stepping motor, a linear motor or a gear motor is used as an electric motor drive for moving the dispensing cone.

A comparatively simple safety concept can be achieved according to another preferred embodiment. A monitoring of the angular position of the drive shaft of an electric motor drive is preferably achieved by way of a two-channel monitoring, with two angle sensors or an angle sensor and an incremental sensor being selectively used.

According to the present invention, the actuation of the electric motor drive as well as the analysis of the measured signals, especially the angle measurements, are carried out in a central control unit by means of a microprocessor. For this purpose, the desired value of the anesthetic concentration, which is input via an input unit directly at the anesthetic dispensing device or an input unit provided at an anesthesia apparatus, is fed as an input variable to the central control unit. If the input unit of an anesthesia apparatus is used, to which the anesthetic dispensing device is fastened at least at times, the desired value is transmitted via a suitable data interface.

The central control unit of an anesthetic dispensing device designed according to the present invention is either an integral component of this device, which is then connected to an anesthesia apparatus via a suitable interface, or else the control of the anesthetic dispensing is integrated into an anesthesia apparatus, especially in the control unit thereof.

At least one temperature-specific correction factor is taken into account by the central control unit in each case in the generation of a control signal, such that temperatures changes, especially those that are caused by the evaporation of anesthetic in the evaporation chamber, are taken into account in the electric motor driven adjustment of a dispensing gap.

According to another embodiment of the present invention, a heating element is provided for the heating of the evaporation chamber at least at times. Such a heating device may be designed, e.g., in the form of a heating element integrated into a wick. In this case, the control signal is preferably generated for adjusting the valve opening, taking a control signal for the heating element into account. As an alternative or in addition a control signal may be generated for the heating element taking into account an adjustment of the valve opening and/or of the control signal for adjusting the valve opening. In this case also, it is, in contrast to conventional anesthetic evaporators, possible to carry out the splitting of the carrier gas stream into a partial gas stream flowing through the bypass channel and a partial gas stream flowing through the dispensing channel exclusively by means of a specific adjustment of the dispensing gap, i.e., especially without having to adjust the bypass gap indirectly or directly as a function of a change in temperature. This can, above all, be attributed to the fact that the influence of the temperature-dependent saturation concentration in the evaporation chamber can be compensated by an automatic change in the dispensing gap. This heating element, which is additionally provided according to this special embodiment, preferably combined with a coupled actuation of the heating element and the valve element, counteracts a cooling off of the evaporation chamber and in this way supports temperature compensation, such that comparatively high evaporation outputs and the increases in the anesthetic concentration connected therewith can also be achieved. Above all, rapid changes can also take place in a comparatively large area.

The present invention is explained in detail below based on special embodiments without limiting the general idea of the present invention on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
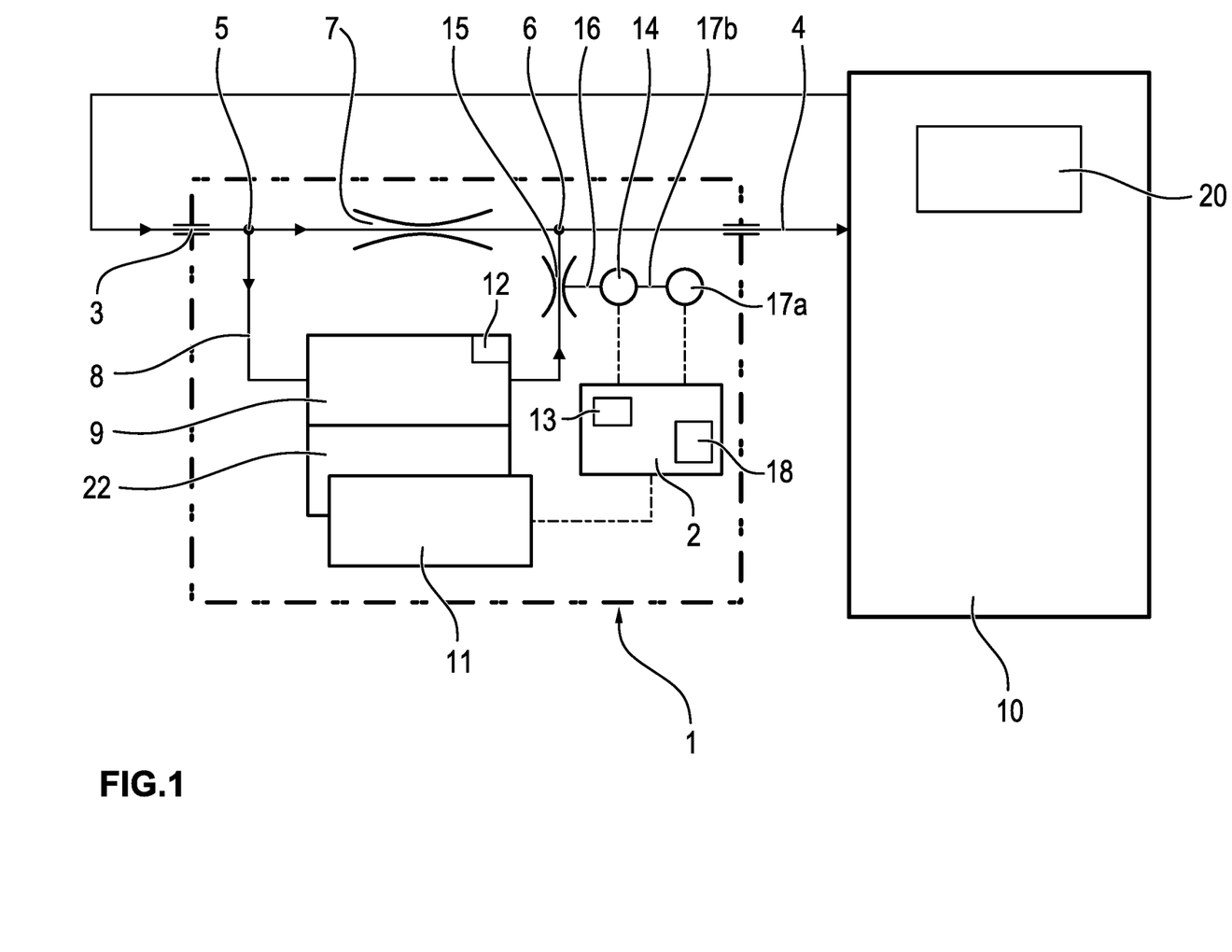
FIG. 1 is schematic view showing a flow path of an anesthetic dispensing device designed according to the present invention with integrated control unit.

Referring to the drawings, FIG. 1 shows a schematic view with flow diagram of an anesthetic dispensing device 1 designed according to the present invention, which can be fastened to an anesthesia apparatus 10. The anesthetic dispensing device 1 has a central control unit 2, by means of which the dispensing of anesthetic in a gas stream as needed is ensured. A data link between the anesthetic dispensing device 1 with integrated control unit 2, on the one hand, and the anesthesia apparatus 10, on the other hand, is not shown.

The carrier gas, especially oxygen-enriched air, flows via a suitable, fluid-tight connection from the anesthesia apparatus 10 into the carrier gas inlet 3 of the anesthetic dispensing device 1. In the area of the carrier gas inlet 3 is located a branch 5, at which the carrier gas stream is split into two partial gas streams, which flow, on the one hand, into a bypass channel 7 and, on the other hand, into a dispensing channel 8. The part of the carrier gas stream, which flows through the bypass channel 7, reaches a mixing point 6 in the area of the anesthetic gas outlet 4 of the anesthetic dispensing device 1 in an unchanged state. At this mixing point 6, the part of the carrier gas stream left unchanged is mixed with the partial gas stream, which has flowed through the dispensing channel 8 and has been enriched with anesthetic in an evaporation chamber 9, such that a gas mixture, which has the needed anesthetic concentration is provided as anesthetic gas at the anesthetic gas outlet 4.

The partial gas stream of the carrier gas, which flows into the dispensing channel 8, is fed to an evaporation chamber 9, in which liquid anesthetic is stored. In the evaporation chamber a wick is provided, which, on the one hand, dips into the liquid anesthetic, and, on the other hand, around which gas to be enriched with anesthetic flows, such that this gas is finally enriched with the necessary quantity of anesthetic. A saturation concentration with anesthetic is adjusted within the evaporation chamber in relation to the gas stream flowing through the evaporation chamber 9. The gas saturated with anesthetic flows from the evaporation chamber 9 through the second section of the dispensing channel 8 to the mixing point 6, where it is mixed with the partial gas stream left unchanged, which has flowed through the bypass channel 7, such that a gas mixture, which has the needed anesthetic concentration, leaves the anesthetic dispensing device 1 via the anesthetic gas outlet 4. This anesthetic gas flows to the anesthesia apparatus 10 and from here finally to the patient via a suitable patient connecting piece.

Figure 6:
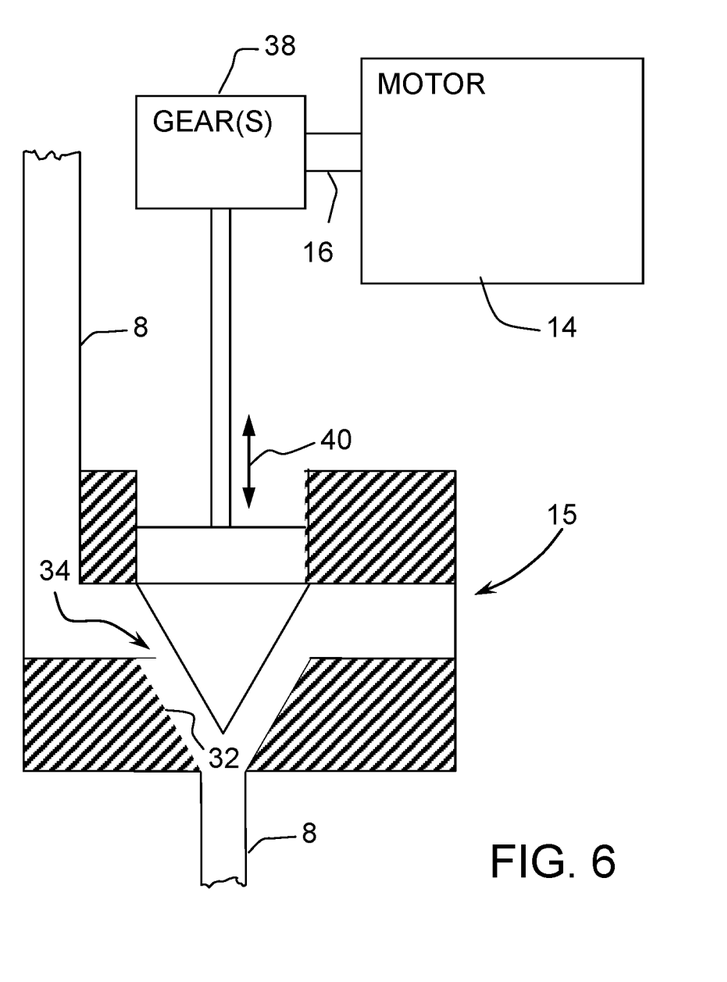
FIG. 6 is a schematic partially sectional view of a valve element with cone-shaped adjusting element and cone sleeve valve seat.

The anesthetic concentration needed is input by the operator, especially an anesthesiologist, via an input unit 11 of the anesthetic dispensing device 1 and made available to the central control unit 2. Further, a temperature sensor 12 is provided, which detects the temperature in the interior of the evaporation chamber 9 and also transmits the corresponding measured values to the central control unit 2 of the anesthetic dispensing device 1. Taking into account the desired concentration of the anesthetic as well as the temperature prevailing in the evaporation chamber 9, a control signal is generated by means of a characteristic stored in a memory 13, with which an electric motor drive 14 can be controlled for adjusting a valve element 15 arranged within the dispensing channel 8, by means of which valve element 15 the gas stream flowing through the evaporation chamber 9 can be affected. The valve element 15 has a cone-shaped adjusting element 30, which can be moved (in the directions of arrows 40) relative to a valve seat designed as a cone sleeve 32 (FIG. 6). A ring-shaped dispensing gap 34, which can be changed as needed and which guarantees an accurate dispensing of anesthetic into the carrier gas stream, is provided by means of such a dispensing cone 30. To implement the necessary adjustment of the dispensing means concentration, by means of such a dispensing cone 30, the angular position of the motor shaft 16 in active connection with the dispensing cone is especially monitored. Such a motor shaft 16 can selectively be used directly or via the intermediary of a gear or gears 38 connected to the dispensing cone 30.

The volume flow or partial gas stream flowing through the dispensing channel 8 and thus through the evaporation chamber 9 can be adjusted as needed in relation to the total volume flow of the carrier gas at the carrier gas inlet 3 by means of the valve element 15, which is arranged in the dispensing channel 8, preferably directly behind the evaporation chamber 9.

The valve unit 15 is designed in the form of a dispensing cone, which can be moved in relation to a dispensing sleeve and by means of which a dispensing opening in the form of a ring gap is made available because of a specific movement of the cone. The dispensing cone is connected to the motor shaft 16 of an electric motor 14, here of a stepping motor, such that the desired dispensing gap and the necessary valve opening is brought about by means of the motor by a movement of the dispensing cone. The control signal, in order to bring about a suitable movement of the dispensing cone, is generated by means of the central control unit 2. In this case, the control signal is generated by taking into account (as a function of) the desired anesthetic concentration, adjusted via the input unit 11. Further, the temperature prevailing in the evaporation chamber 9 and detected by the temperature sensor 12 is taken into account in the generation of the control signal (the control signal is also a function of the temperature prevailing in the evaporation chamber 9). A temperature compensation value, which is finally used as a basis for generating the control signal, is determined by means of the measured temperature and a characteristic stored in the memory 13. As soon as the control signal is generated in the manner described above, the dispensing cone provided as the valve element 15 is adjusted and the dispensing gap is adjusted to the desired value.

According to the present invention, the valve gap, which is in the form of a ring gap here, is thus adjusted between the dispensing cone and the cone sleeve by means of a specifically actuated electric motor 14. In this case, the dispensing elements usually used for adjusting the anesthetic concentration, such as the bypass and the dispensing cone as well as the evaporation chamber 9, are designed as in the prior-art anesthetic dispensing devices. By means of this measure, it is possible to provide a comparatively simple safety concept, in which only the angular position of the drive shaft and of the motor shaft 16 of the electric motor 14 connected rigidly to the dispensing cone have to be monitored by means of a sensor 17. A two-channel monitoring is carried out in this case either with two angle sensors 17a or an angle sensor 17a and an incremental sensor 17b.

The electric motor 14 used is a stepping motor, which is connected to the drive shaft of the dispensing cone for reinforcing the torque via a gear. The actuation of the electric motor 14 as well as the analysis of the angle values detected take place by means of the central control unit 2, especially by means of a microprocessor 18, which first receives, as an input variable, the desired value of the necessary anesthetic concentration via the input unit 11 of the anesthetic dispensing device 1. Further, at least one temperature-specific correction factor and thus temperature-related effects on the valve element 15 are taken into account for generating a control signal for the electric motor 14.

Figure 2:
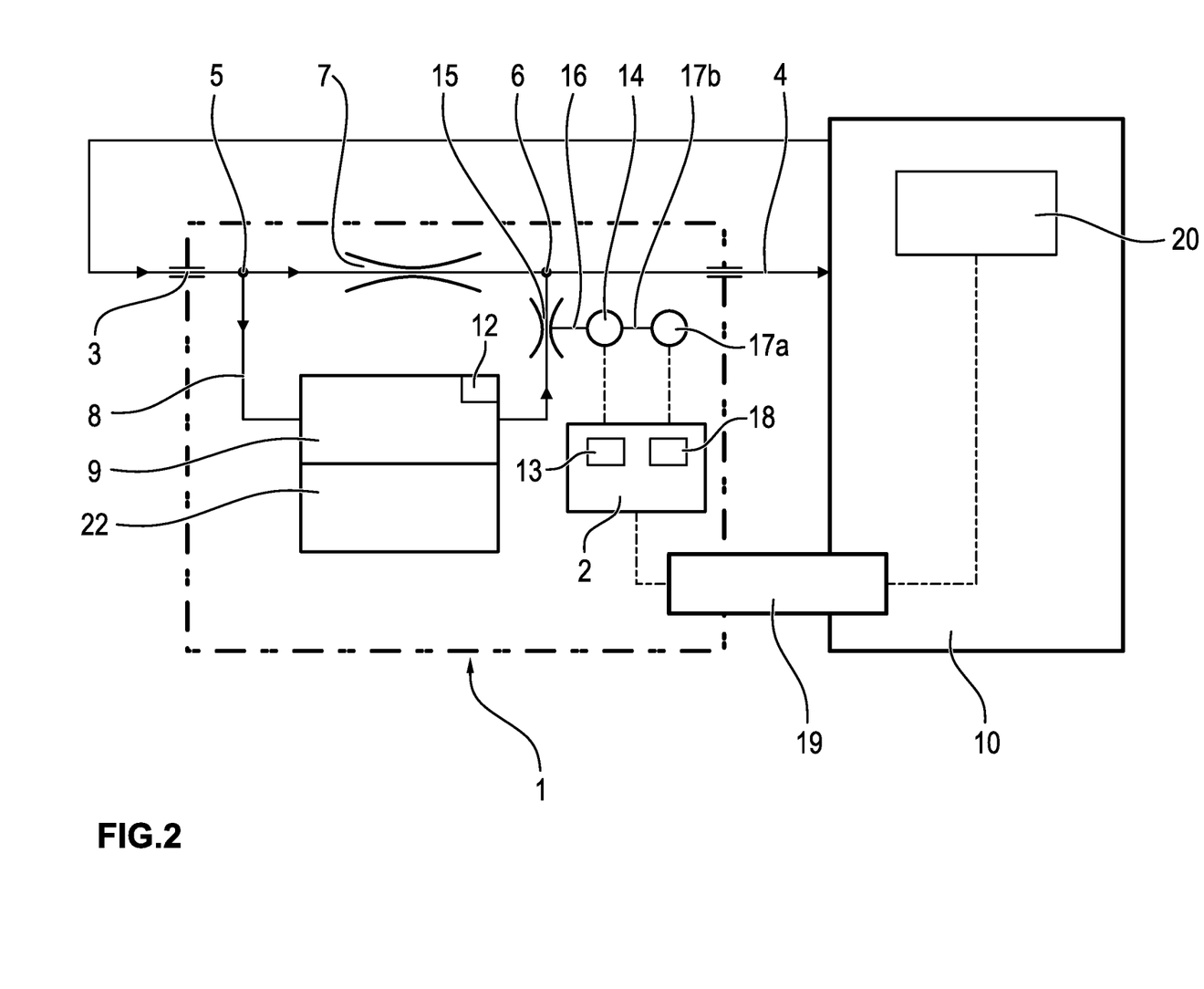
FIG. 2 is a schematic view showing a flow path of an anesthetic dispensing device designed according to the present invention with control unit, which is connected to the anesthesia apparatus via an interface.

FIG. 2 shows another schematic view with flow diagram of an anesthetic dispensing device designed according to the present invention. The essential components of the anesthetic dispensing device described in connection with FIG. 2 correspond to the components, which were explained above in connection with FIG. 1. Identical components are identified with identical reference numbers.

The essential difference between the anesthetic dispensing devices 1 shown in FIG. 2 and in FIG. 1 is that according to FIG. 2 the anesthetic dispensing device 1 itself does not have an input unit, but rather an interface 19 is provided, via which the anesthetic dispensing device 1 is connected to the anesthesia apparatus 10 in terms of data. In this case, the desired value for the desired concentration of the anesthetic in the anesthetic gas is input via an input unit 20 provided at the anesthesia apparatus 10 and this value is fed as a desired value via the interface 19 of the central control unit 2 of the anesthetic dispensing device 1. In the central control unit 2 of the anesthetic dispensing device 1, a control signal is generated for an electric motor 14 on the basis of (as a function of) this desired value as well as an apparatus-specific temperature compensation value, which was determined on the basis of a characteristic stored in a memory 13. By means of the electric motor 14 actuated in this way, the dispensing cone of a valve element 15 is in turn moved in such a way that the necessary volume flow flows through the evaporation chamber 9 of the anesthetic dispensing device 1 and is finally mixed in the mixing point 6 with the carrier gas stream leaving the bypass channel 7. It is essential in turn that at least one temperature-specific correction factor and thus temperature-related effects on the valve element 15 are taken into account for generating a control signal for the electric motor 14 connected to the valve element 15. At least one sensor 17, which detects a movement of the motor driven shaft or the valve drive shaft and transmits this value to the central control unit 2 of the anesthetic dispensing device 1, is in turn provided for monitoring the adjusting operation. In this way, a comparatively simple monitoring of the adjusting operation and thus of the anesthetic dispensing is achieved.

Figure 3:
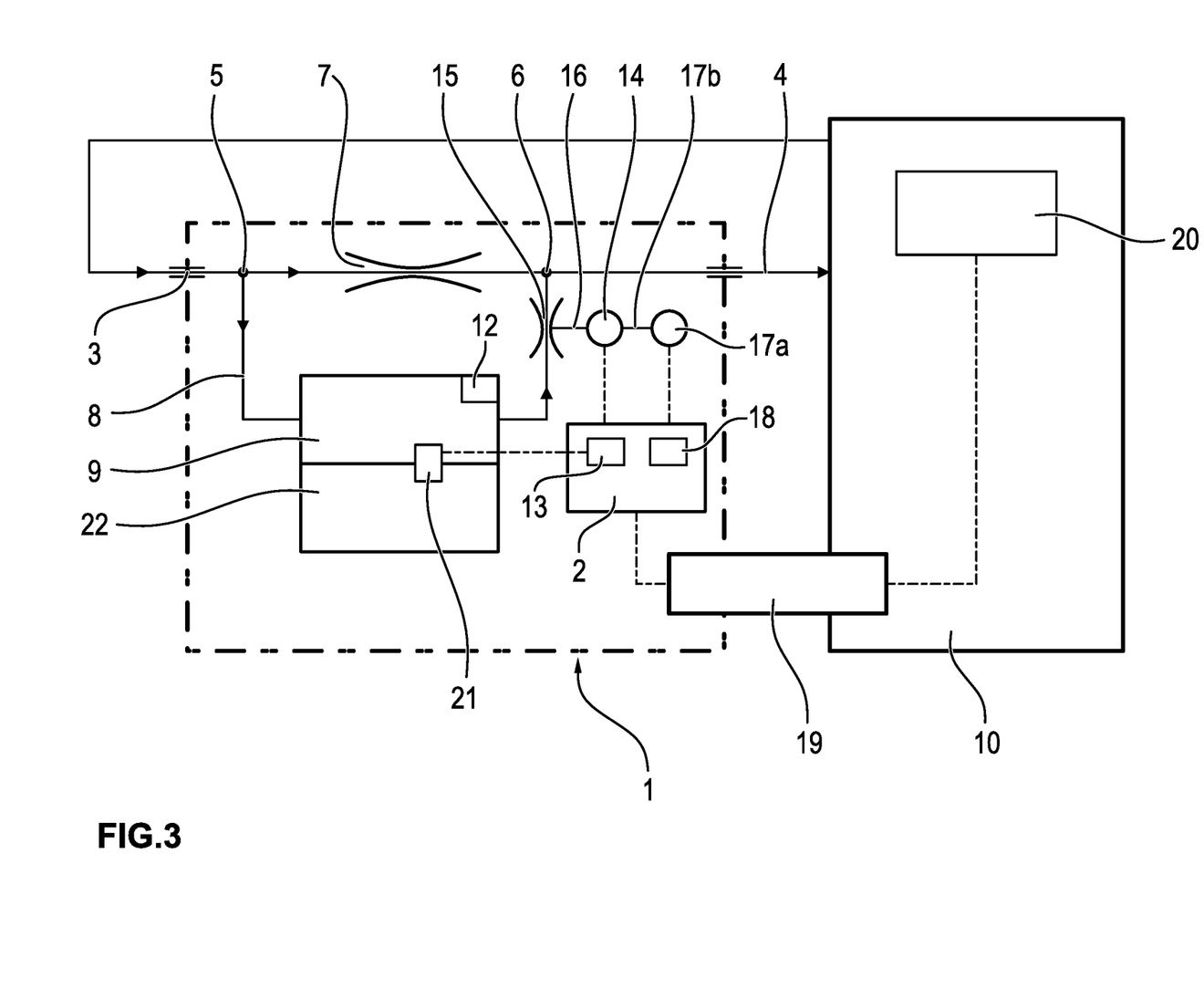
FIG. 3 is a schematic view showing a flow path of an anesthetic dispensing device designed according to the present invention with heatable evaporation chamber and with control unit, which is connected to an anesthesia apparatus via an interface.

FIG. 3 shows a schematic view with a flow chart of an anesthetic dispensing device designed according to FIG. 2, which, however, has a special evaporation chamber 9. The control unit 2 of the anesthetic dispensing device 1 is in turn connected to an anesthesia apparatus 10 via a data interface 19, such that desired values for the anesthetic concentration can be transmitted via an input unit 20 of the anesthesia device to the control unit 2 of the anesthetic dispensing device.

In the exemplary embodiment shown in FIG. 3, the evaporation chamber has a heating element 21, via which the evaporation in the evaporation chamber 9 can be affected by a specific heat input. The heating element 21 is an electrical hot wire, which is integrated into the wick of the evaporation chamber 9. In the central control unit 2 of the anesthetic dispensing device 1, a corresponding control signal is generated for this, and this control signal and the corresponding heat input in the evaporation chamber 9 are taken into account in the generation of a control signal for the electric drive 14 for adjusting the valve element 15.

Since the central control unit 2 present in the anesthetic dispensing device 1 also takes charge of the control of the heating element 21 in the wick, the temperature measured in the evaporation chamber 9 with the temperature sensor 12 can be taken into account in the dispensing of anesthetic. This technical design also makes possible the use of a simple bypass gap, which is kept constant in contrast to the conventional anesthetic evaporators, since the effect of temperature-dependent saturation concentration in the evaporation chamber can be compensated by an automatic change in the dispensing gap. Thus, no additional adjusting valve or butterfly valve, which brings about a suitable splitting of the carrier gas stream into corresponding partial gas streams, is necessary.

Figure 4:
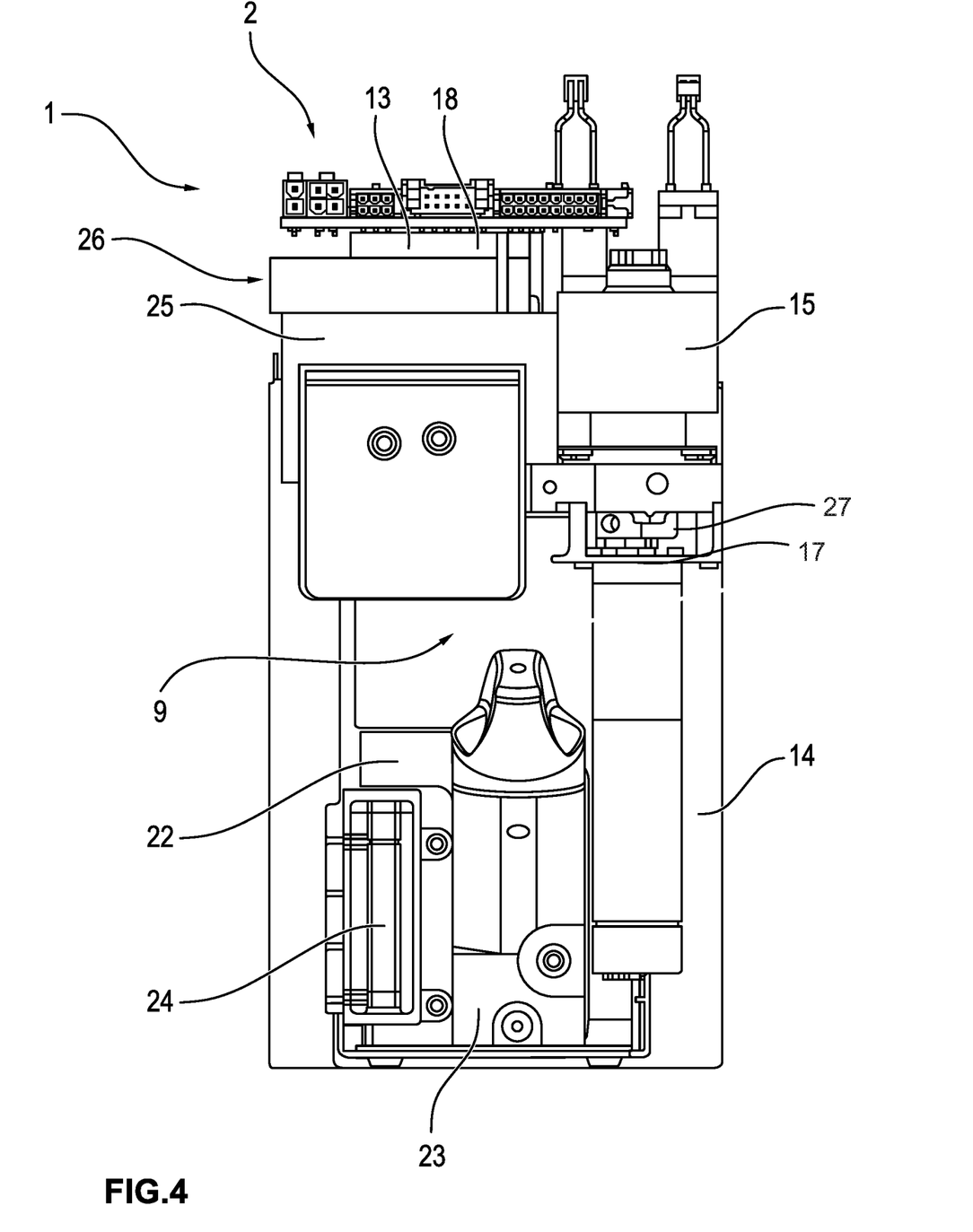
FIG. 4 is a view of the anesthetic dispensing device showing the evaporation chamber with electric motor driven dispensing unit.

FIG. 4 shows in a front view an anesthetic dispensing device 1 designed according to the present invention, which has a valve element 15 driven by means of an electric motor 14 for adjusting the gas stream flowing through the evaporation chamber 9. The essential components of the anesthetic dispensing device 1 are an anesthetic tank 22, in which liquid anesthetic is stored, a wick, via which liquid anesthetic in an evaporation chamber 9 is fed to a gas stream to be enriched with anesthetic, as well as an electric motor driven valve element 15, by means of which the volume flow of the gas flowing through the evaporation chamber can be adjusted. The electric drive 14 is designed here as a gear motor, i.e., as a combination of an electric motor and a gear which ensures that the drive shaft of the valve element 15 is rotated at a slower speed, but with considerably higher torque than the driven shaft of the motor 14. The gear driven shaft in this case is in active connection with a valve element 15 with a dispensing cone, such that a dispensing gap in the form of a ring gap can be adjusted between the dispensing cone and a cone sleeve in a specific manner. The gear motor 14 is actuated by means of a central control unit 2. The central control unit 2 here can be connected via a data interface 19 to the input unit 20 of an anesthesia apparatus 10. Via this input unit, it is possible for an operator, especially an anesthesiologist, to adjust a value for the anesthetic concentration needed in each case, which is then made available as a desired value to the control unit 2 of the anesthetic dispensing device 1.

The control unit 2 is connected to a memory 13, in which apparatus-specific characteristics are stored for the compensation of temperature changes in the evaporation chamber 9. Depending on the temperature in the evaporation chamber 9 of the anesthetic dispensing device 1, which is detected by means of a suitable temperature sensor 12, a temperature compensation value, which together with the desired value for the desired anesthetic concentration is taken into account in the generation of a control signal for the gear motor 14, is determined by taking into account the recorded characteristic. Finally, the control signal generated brings about the adjustment of the valve element 15 by means of the gear motor 14, such that the dispensing gap is adjusted to the desired value and a corresponding volume flow flows through the evaporation chamber 9. The angular position of the driven shaft of the gear motor, which corresponds to the drive shaft of the valve element 15, is detected with a sensor 17 and this value is transmitted to the central control unit 2. As soon as the angular position of the driven shaft corresponds to the desired opening of the dispensing gap, the movement of the motor 14 is stopped. Based on this monitoring concept, an accurate adjustment of the valve element 15 and thus of the anesthetic concentration in the anesthetic gas can be ensured in a comparatively simple manner and the corresponding values can also be kept constant over a long time.

Further, a mechanical stop 27 for the cone is provided as an additional, independent safety element to prevent a blocking state of the cone, in which this [cone] brings the dispensing gap to a stop, and damage of the cone usually connected therewith, in case of an error independently of the angle sensors. Furthermore, the mechanical stop can be used to accurately determine the zero position of the cone, i.e., the zero point for the angle measurement, in order to thus increase the accuracy of the angle adjustment. In this way, it is further possible to use incremental sensors which do not determine an absolute angle value.

Figure 5:
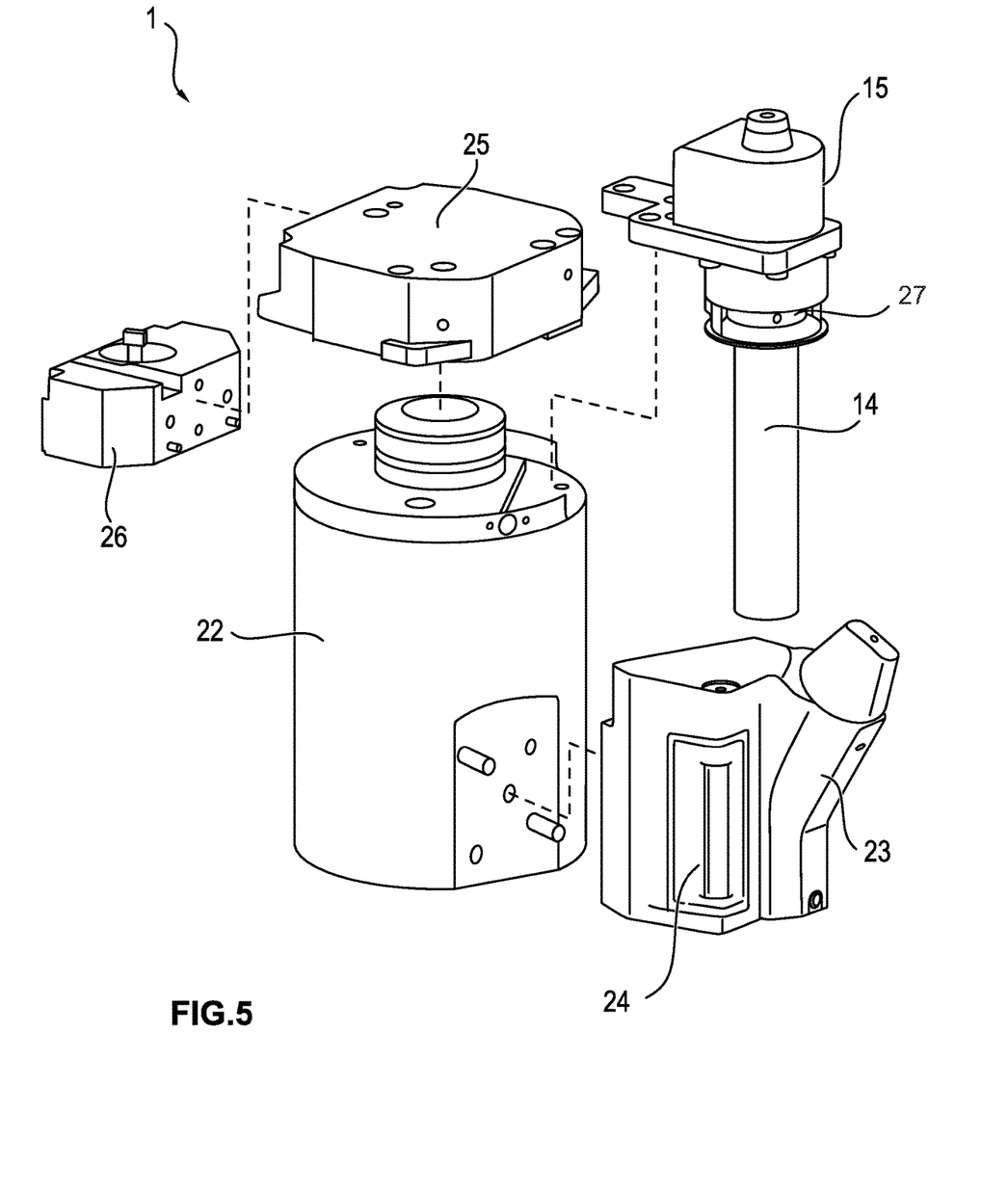
FIG. 5 is an exploded view of the anesthetic dispensing device showing with the electric motor driven dispensing unit.

FIG. 5 again shows the essential components of an anesthetic dispensing device 1 designed according to the present invention. A filling module 23, via which the anesthetic needed in each case can be filled, can be fastened to the anesthetic tank 22. The filling level of the anesthetic can be monitored here via an indicator 24 provided in the front area of the anesthetic dispensing device 1. The so-called bypass cover 25 is fastened in the upper area of the anesthetic tank 22. In this bypass cover 25, the carrier gas flows into the dispensing unit 1 in the operating state from the pneumatic module 26. The branch 5, at which the dispensing channel 8 branches in the direction of the evaporation chamber 9, is located in the bypass cover 25. The mixing point 6, in which the unchanged partial gas stream flowing through the bypass channel 7 as well as the partial gas stream enriched with anesthetic are mixed to form an anesthetic gas, which has the desired anesthetic concentration, is also arranged in the bypass cover 25. The anesthetic gas finally leaves the anesthetic dispensing device 1 in turn via the pneumatic module 26 and flows from here through the anesthesia apparatus 10, to which the anesthetic dispensing device 1 is fastened, to the patient.

While specific embodiments of the invention have been shown and described in detail to illustrate the application of the principles of the invention, it will be understood that the invention may be embodied otherwise without departing from such principles.

APPENDIX

List of Reference Numbers

1 Anesthetic dispensing device
2 Control unit
3 Carrier gas inlet unit/anesthesia apparatus
4 Anesthetic gas outlet
5 Branch
6 Mixing point
7 Bypass channel
8 Dispensing channel
9 Evaporation chamber
10 Anesthesia apparatus
11 Input unit of the anesthetic dispensing device
12 Temperature sensor
13 Memory
14 Electric motor
15 Valve element
16 Motor shaft
17 Sensor for detecting movement
   17a Angle sensor
   17b Incremental sensor
18 Microprocessor
19 Data interface of dispensing
20 Input unit of the anesthesia apparatus
21 Heating element
22 Anesthetic tank
23 Filling module
24 Filling level indicator
25 Bypass cover
26 Pneumatic module
27 Safety stop

What is claimed is:

1. An anesthetic dispensing device comprising:
a carrier gas inlet;
a bypass channel;
a dispensing channel arranged parallel to the bypass channel with respect to fluid flow;
an anesthetic gas outlet connected to the carrier gas inlet via the bypass channel and via the dispensing channel;
an evaporation chamber providing an anesthetic, the evaporation chamber being supplied from the dispensing channel with a gas, which is enriched with an anesthetic in the evaporation chamber, such that gas enriched with anesthetic flows from the evaporation chamber to a mixing point, in which the gas enriched with anesthetic is mixed with gas coming from the bypass channel to form anesthetic gas, which flows to the anesthetic gas outlet;
a valve element having a valve opening which is changed to vary a volume flow of gas to be enriched with anesthetic that is flowing through the evaporation chamber;

a temperature sensor configured for detecting a temperature in an interior of the evaporation chamber and a surrounding area temperature of the evaporation chamber;

an electric motor drive for adjusting the valve opening of the valve element; and a control unit generating a control signal for controlling the electric motor drive on the basis of a concentration of the anesthetic in the anesthetic gas needed at the anesthetic gas outlet and at least one temperature-specific correction factor corresponding to an apparatus specific characteristic of the anesthetic dispensing device, the temperature-specific correction factor being formed by taking into account an absolute temperature and a temperature change in an area surrounding the dispensing device, and an absolute temperature and a temperature change in the evaporation chamber, a memory unit, wherein the control unit is connected to the memory unit, in which the apparatus specific characteristic is stored for determining the temperature-specific correction factor.

2. An anesthetic dispensing device in accordance with claim 1, wherein the temperature sensor transmits the detected values at least indirectly to the control unit, wherein the temperature sensor is arranged at least in some areas in or at the evaporation chamber, whereby the temperature-specific correction factor is generated taking the detected value into account.

3. An anesthetic dispensing device in accordance with claim 1, wherein the valve opening is designed in the form of a changeable ring gap.

4. An anesthetic dispensing device in accordance with claim 1, wherein the valve element has a cone mounted movably with respect to a cone-shaped sleeve.

5. An anesthetic dispensing device in accordance with claim 1, wherein the electric motor drive comprises one of a stepping motor, a linear motor and a gear motor.

6. An anesthetic dispensing device in accordance with claim 1, wherein the control unit is integrated into an anesthesia apparatus or an interface is provided for the transmission of data between the control unit and an anesthesia apparatus.

7. An anesthetic dispensing device in accordance with claim 1, further comprising a heating element for heating the evaporation chamber at least at times.

8. An anesthetic dispensing device in accordance with claim 7, wherein a control signal is generated in the control unit for adjusting the valve opening, taking a control signal for the heating element into account.

9. An anesthetic dispensing device in accordance with claim 7, wherein a control signal is generated for the heating element, taking into account at least one of an adjustment of the valve opening and of a control signal for adjusting the valve opening.

10. An anesthetic dispensing device in accordance with claim 1, further comprising a stop limiting a movement of the valve element in at least one direction of movement.

11. An anesthetic dispensing device in accordance with claim 1, wherein:
the apparatus specific characteristic takes into account temperature-related effects on the valve element.

12. An anesthetic dispensing device comprising:
a flow arrangement comprising a bypass channel, a dispensing channel arranged parallel to the bypass channel with respect to fluid flow, a carrier gas inlet and an anesthetic gas outlet connected to the carrier gas inlet via the bypass channel and via the dispensing channel;

an evaporation chamber with an anesthetic reservoir, the evaporation chamber being in fluidic connection with the dispensing channel to enrich gas with an anesthetic in the evaporation chamber, such that gas enriched with anesthetic flows from the evaporation chamber to a mixing point, in which the gas enriched with anesthetic is mixed with gas coming from the bypass channel to form anesthetic gas, which flows to the anesthetic gas outlet;

a valve element having a variable valve opening which is changed to vary a volume flow of gas to be enriched with anesthetic that is flowing through the evaporation chamber;

a temperature sensor configured for detecting a temperature in an interior of the evaporation chamber and a surrounding area temperature of the evaporation chamber;

an electric motor drive connected to the valve element and adjusting the valve opening of the valve element; and a control unit generating a control signal for controlling the electric motor drive as a function of a concentration of the anesthetic in the anesthetic gas needed at the anesthetic gas outlet and as a function of at least one temperature-specific correction factor corresponding to an apparatus specific characteristic of the anesthetic dispensing device, the temperature-specific correction factor being formed by taking into account an absolute temperature and a temperature change in an area surrounding the dispensing device, and an absolute temperature and a temperature change in the evaporation chamber, a memory unit, wherein the control unit is connected to the memory unit, in which the apparatus specific characteristic is stored for determining the temperature-specific correction factor.

13. An anesthetic dispensing device in accordance with claim 12, wherein the temperature sensor the detected values at least indirectly to the control unit, wherein the temperature sensor is arranged at least in some areas in or at the evaporation chamber, whereby the temperature-specific correction factor is generated taking the detected value into account.

14. An anesthetic dispensing device in accordance with claim 12, in combination with an anesthesia apparatus wherein the control unit is integrated into the anesthesia apparatus or an interface is provided for the transmission of data between the control unit and the anesthesia apparatus.

15. An anesthetic dispensing device in accordance with claim 12, further comprising a heating element for heating the evaporation chamber at least at times, wherein a control signal is generated in the control unit for adjusting the valve opening, taking a control signal for the heating element into account and a control signal is generated for the heating element, taking into account at least one of an adjustment of the valve opening and of a control signal for adjusting the valve opening.

16. An anesthetic dispensing device in accordance with claim 12, wherein:
the apparatus specific characteristic takes into account temperature-related effects on the valve element.

17. An anesthetic dispensing device comprising:
a carrier gas inlet configured to receive a carrier gas;
a bypass channel configured to receive the carrier gas from said carrier gas inlet;
a dispensing channel configured to receive the carrier gas from said carrier gas inlet;

an evaporation chamber configured to receive the carrier gas from said dispensing channel, said evaporation chamber configured to provide an anesthetic to the carrier gas;

a temperature sensor configured for detecting a temperature in an interior of the evaporation chamber;

a valve element configured to receive the carrier gas with the anesthetic from said evaporation chamber, said valve element being configured to selectively vary a flow of the carrier gas flowing through said evaporation chamber;

an anesthetic gas outlet configured to receive the carrier gas from said bypass channel and receive the carrier gas with the anesthetic from said valve element, said evaporation chamber and said valve element being arranged in parallel with said bypass channel;

an electric motor drive for selectively adjusting said valve element; and a control unit generating a control signal for controlling said electric motor drive as a function of a predetermined concentration of the anesthetic desired in the carrier gas at said anesthetic gas outlet, and as a function of a temperature-specific correction factor corresponding to an apparatus specific characteristic of the anesthetic dispensing device, the temperature-specific correction factor being formed by taking into account an absolute temperature and a temperature change in an area surrounding the dispensing device and the evaporation chamber, the apparatus specific characteristic takes into account temperature-related effects on the valve element from the absolute temperature and the temperature change in the area surrounding the dispensing device and the evaporation chamber.

* * * * *